(12) United States Patent
Billman et al.

(10) Patent No.: US 10,119,884 B1
(45) Date of Patent: Nov. 6, 2018

(54) WATER DETECTION ASSEMBLY

(71) Applicant: United Services Automoblie Association (USAA), San Antonio, TX (US)

(72) Inventors: Bradly Jay Billman, Celina, TX (US); Kade Scott, The Colony, TX (US); Matthew T. Flachsbart, Grapevine, TX (US); Cory Matheson, Cellina, TX (US); Benjamin D. Ethington, Fruit Heights, UT (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 15/636,270

(22) Filed: Jun. 28, 2017

Related U.S. Application Data

(60) Provisional application No. 62/461,653, filed on Feb. 21, 2017, provisional application No. 62/401,522, filed on Sep. 29, 2016, provisional application No. 62/355,732, filed on Jun. 28, 2016.

(51) Int. Cl.
  *G01M 3/40* (2006.01)
  *G01N 27/04* (2006.01)
  *G08B 21/20* (2006.01)

(52) U.S. Cl.
  CPC ............ *G01M 3/40* (2013.01); *G01N 27/048* (2013.01); *G08B 21/20* (2013.01)

(58) Field of Classification Search
  CPC ........ G01M 3/40; G01N 27/048; G08B 21/20
  USPC ....................................................... 340/604
  See application file for complete search history.

(56) References Cited

U.S. PATENT DOCUMENTS

| | | | | |
|---|---|---|---|---|
| 2002/0186141 A1* | 12/2002 | Jen | ......................... | G08B 17/10 340/630 |
| 2009/0315720 A1* | 12/2009 | Clement | ................. | A61F 13/42 340/573.5 |

* cited by examiner

*Primary Examiner* — Kerri L McNally
(74) *Attorney, Agent, or Firm* — Fletcher Yoder, P.C.

(57) ABSTRACT

The present disclosure relates to a water detection device that includes a water-activated battery configured to switch from a dormant condition to an active condition upon contact with water, such that the water-activated battery supplies an electrical voltage upon contact with the water, an electronic circuit configured to receive the electrical voltage from the water-activated battery, where the electronic circuit is configured to communicate with an external, electronic device via one or more wireless communication techniques when the electronic circuit is powered by the electrical voltage, and where communication between the electronic circuit and the external, electronic device is an uninterrupted communication when the electronic circuit is receiving the electrical voltage from the water-activated battery, and a housing configured to receive the water-activated battery and the electronic circuit, where the housing has passageways configured to facilitate movement of the water into the housing and toward the battery.

19 Claims, 11 Drawing Sheets

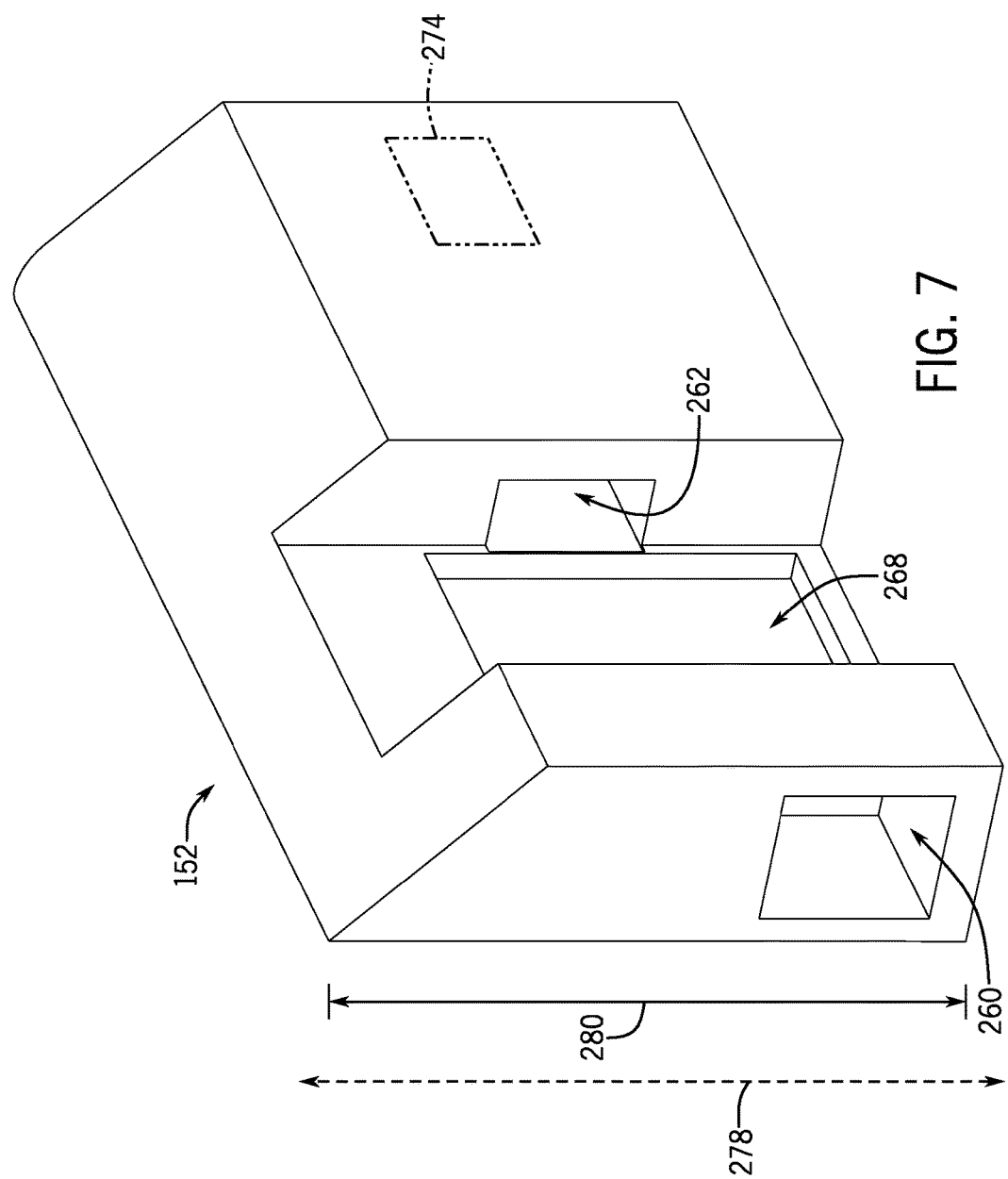

WATER DETECTION ASSEMBLY

CROSS REFERENCE TO RELATED APPLICATIONS

This application claims priority from and the benefit of U.S. Provisional Application Ser. No. 62/355,732, entitled "WATER DETECTION SENSOR WITH A WATER ACTIVATED BATTERY," filed Jun. 28, 2016, U.S. Provisional Application Ser. No. 62/401,522, entitled "WATER DETECTION SENSOR WITH A WATER ACTIVATED BATTERY," filed Sep. 29, 2016, and U.S. Provisional Application Ser. No. 62/461,653, entitled "WATER DETECTION ASSEMBLY," filed Feb. 21, 2017, which are hereby incorporated by reference in their entireties.

BACKGROUND

The present disclosure relates generally to a water detection device.

Water damage leads to common claims on property insurance policies. Early detection of water leaks can substantially lessen the severity of water damage. However, leaks often occur in pipes that are hidden behind walls or in cracks in foundations or other fluid pathways that are not readily observable. When the leaks are eventually observed, significant damage may have occurred. It is therefore desirable to place water detection devices in locations where leaks may occur to provide warning to designated people of a detection event so they can take corrective action immediately or to signal another device to take corrective action, such as shutting a water supply valve.

SUMMARY

The present disclosure relates to a water detection device that includes a water-activated battery configured to switch from a dormant condition to an active condition upon contact with water, such that the water-activated battery supplies an electrical voltage upon contact with the water, an electronic circuit configured to receive the electrical voltage from the water-activated battery, where the electronic circuit is configured to communicate with an external, electronic device via one or more wireless communication techniques when the electronic circuit is powered by the electrical voltage, and where communication between the electronic circuit and the external, electronic device is an uninterrupted communication when the electronic circuit is receiving the electrical voltage from the water-activated battery, and a housing configured to receive the water-activated battery and the electronic circuit, where the housing has passageways configured to facilitate movement of the water into the housing and toward the battery.

The present disclosure further relates to a water detection device that includes a water-activated battery to switch from a dormant condition to an active condition upon contact with water, such that the water-activated batter supplies an electrical voltage upon contact with the water, an electronic circuit configured to receive the electrical voltage from the water-activated battery, where the electronic circuit is configured to communicate with an external, electronic device via one or more wireless communication techniques when the electronic circuit is powered by the electrical voltage, and where communication between the electronic circuit and the external, electronic device is an uninterrupted communication when the electronic circuit is receiving the electrical voltage from the water-activated battery, an additional battery configured to periodically supply an additional electrical voltage to the electronic circuit, such that communication between the electronic circuit and the external electronic device is intermittent when the water-activated battery is in the dormant condition, and a housing configured to receive the water-activated battery, the electronic circuit, and the additional battery, where the housing includes passageways configured to facilitate movement of the water into the housing and toward the battery.

The present disclosure further relates to a method that includes sending intermittent communications between an electronic circuit of a detection device and an external, electronic device when a water-activated battery electrically coupled to the electronic circuit is in a dormant condition, activating the water-activated battery to switch from the dormant condition to an active condition upon exposure of the water-activated battery to water, supplying an electrical voltage from the water-activated power source to the electronic circuit when the water-activated battery is in the active condition, and sending uninterrupted communications between the electronic circuit and the external, electronic device when the water-activated battery is in the active condition.

DRAWINGS

These and other features, aspects, and advantages of the present disclosure will become better understood when the following detailed description is read with reference to the accompanying drawings in which like characters represent like parts throughout the drawings, wherein:

FIG. 7 is a perspective view of an embodiment of the component housing of FIG. 6 that may be configured to be disposed within the housing of FIGS. 3 and 4, in accordance with an aspect of the present disclosure;

Figure 1:
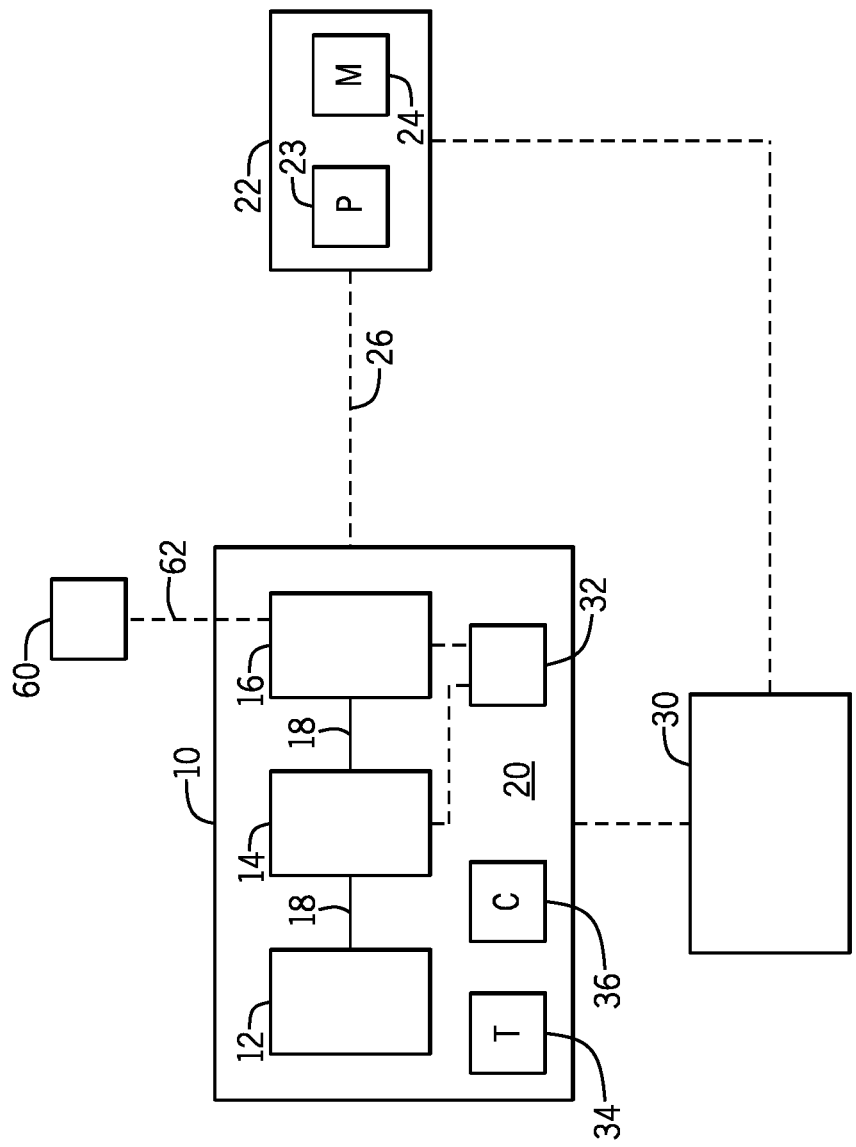
FIG. 1 is a schematic of an embodiment of a water detection device that may be utilized to detect a presence of a fluid, in accordance with an aspect of the present disclosure.
Figure 14:
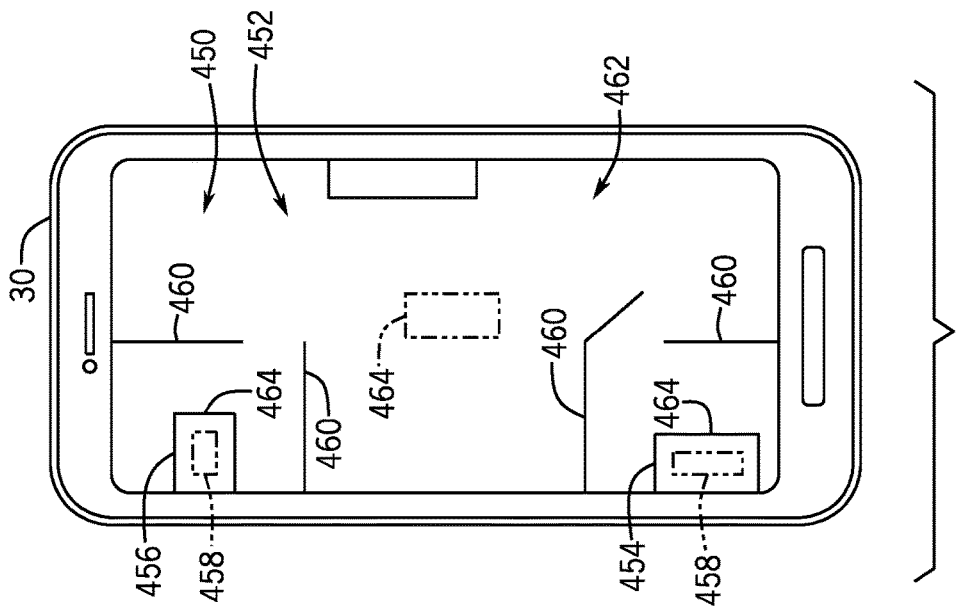
Figure 15:
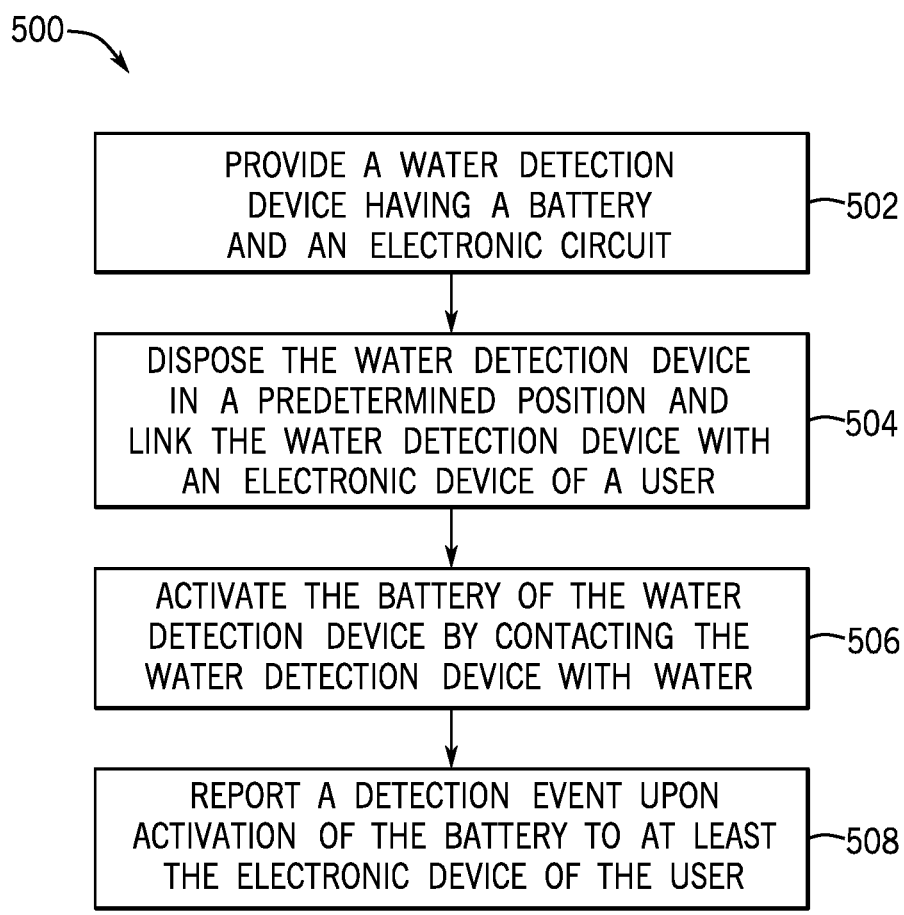

FIG. 14 is a schematic of an embodiment of a fifth user interface on an electronic device that may be utilized with the water detection device of FIG. 1, in accordance with an aspect of the present disclosure; and FIG. 15 is a block diagram of an embodiment of a process that may be utilized to establish a detection event using the water detection device of FIG. 1, in accordance with an aspect of the present disclosure.

DETAILED DESCRIPTION

One or more specific embodiments of the present disclosure are described above. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments are generally directed toward a water detection device (e.g., a water detection assembly) that may be utilized to monitor the presence of water (e.g., leaks, floods, etc.) in a predetermined location, such as a home (e.g., under the sink, in the walls, in the attic, near toilets, near washing machines, near dishwashers, near water heaters, among other locations), a car, a commercial building, and/or other suitable locations. The water detection device may be modular in that certain components (e.g., a communication module, a control feature, a battery, and/or a communication beacon) may be inserted and/or removed from a housing to facilitate replacement of components and/or to facilitate programming of various features of the water detection device.

In some cases, the water detection device may include a water activated battery that generates an electrical voltage upon exposure to water. The water detection device may thus be in a dormant condition (e.g., no signals are sent or received) until water is present in a sufficient amount to activate the battery. The housing of the water detection device may include physical features (e.g., fluid passageways) that may direct water toward the water activated battery, such as capillaries and/or channels that enable water to flow along a target path into the housing and toward the battery. Further, the housing may include a water-soluble coating that may dissolve upon exposure to a predetermined amount of water. Therefore, components in the water detection device housing may be shielded from humidity and/or other contaminants until a sufficient amount of water is present to dissolve the coating and activate the battery.

The water detection device may include the communication beacon which may be configured to communicate with an external electronic device (e.g., a server, the Internet, a computer, a mobile phone, a tablet, etc.) when the battery is activated. For example, upon exposure to water, the battery may be activated and thus supply electronic voltage to the communication beacon, which may then communicate with the external electronic device to notify a user of a detection event (e.g., a leak, a flood, or another event). In some embodiments, the communication beacon may be in communication with the electronic device via software on the electronic device that may be utilized with the water detection device. For instance, the software may be an application on an electronic device (e.g., mobile phone, tablet, computer, or another suitable electronic device) that may be linked (e.g., paired and/or coupled) to the water detection device. The software may enable the user to monitor and manage multiple water detection devices that may be positioned in various locations within a structure (e.g., a home, a commercial building, and/or a vehicle). In any case, the software may alert the user of a detection event when a respective water detection device is activated upon exposure to water.

Turning now to the drawings, FIG. 1 is a schematic of a water detection device 10 (e.g., a water detection assembly) that includes a battery 12 (e.g., a dormant, water-activated battery), an electronic circuit 14 (e.g., a processor and/or other circuitry that may be included in a communication beacon), and memory 16 (e.g., also included in the communication beacon). The battery 12, the electronic circuit 14, and/or the memory 16 may be electronically connected together using solder, a wire, a bus 18, or another suitable technique. Additionally, the battery 12, electronic circuit 14, and/or the memory 16 may be physically coupled to one another by a connector 20 (e.g., a circuit board). In some embodiments, the battery 12, the electronic circuit 14, and/or the memory 16 may be disposed in a common housing (see e.g., FIGS. 3 and 4). Further, the battery 12, the electronic circuit 14, and/or the memory 16 may be modular in design, such that the battery 12, the electronic circuit 14, and/or the memory 16 may be connected, disconnected, and reconnected to one another as desired (e.g., via the housing). The water detection device 10 may also be within communication range of an electronic network 22 (e.g., a server, the Internet, etc.). The network 22 may include a processor 23 and/or memory 24 that may be configured to store instructions that the processor 23 executes. In some embodiments, the water detection device 10 may be configured to communicate with electronic devices (e.g., a computer, a tablet, a mobile phone, or another suitable electronic device), and thus, send and receive information to and from such devices.

In some embodiments, the battery 12 may be water-activated. Therefore, before exposure to water, the battery 12 may be in a dormant condition, such that no signal is transferred to or received from the electronic network 22 by the water detection device 10. However, when the water detection device 10 is exposed to water, the water detection device 10 may be activated to an active condition, such that the water detection device 10 transmits a signal 26 to the network 22 (e.g., via the electronic circuit 14), and ultimately to an electronic device 30 of a user. In some embodiments, the water detection device 10 may communicate directly with the electronic device 30 (e.g., via a Bluetooth feature of the water detection device 10).

The battery 12 (e.g., a water-activated battery) may be capable of remaining dormant for a significant period of time before generating electrical voltage that ultimately supplies power to the electronic circuit 14 and/or the memory 16. Further, in some embodiments, the battery 12 may be dormant for the significant period of time and produce sufficient electrical voltage to power the electronic circuit 14 and/or the memory 16 without charging from a power source. As discussed above, the battery 12 may be water activated, such that the battery 12 remains dormant (e.g., incapable of generating a voltage) until exposed to water, when the battery 12 may then generate the electrical voltage to power the electronic circuit 14 and/or the memory 16. For example, the battery 12 may include a dry material that initiates a chemical reaction when exposed to water. The chemical reaction may then generate the electrical voltage, which may be supplied to the electronic circuit 14 and/or the memory 16 via the bus 18. Suitable dry materials for an anode of the battery 12 include, but are not limited to, magnesium (e.g., magnesium AZ61A, magnesium AZ31B, magnesium AP65 and magnesium MTA75), aluminum, zinc, lead, thallium, manganese, silicon, iron, calcium, nickel, copper, and/or a combination thereof.

Further, the battery 12 may include a cathode and an anode, which may facilitate the chemical reaction. In some embodiments, the cathode may include a depolarizer (e.g., sulfur, additive, binder, wax, a combination thereof, or other suitable materials) and a current collector (e.g., silver chloride, cuprous iodide, cuprous thiocyanate, lead chloride, cuprous chloride, or combinations thereof). The battery 12 may also include separators (e.g., nonconductive spacers) placed between the anode and the cathode to form a space for free ingress of electrolytes and egress of corrosion products. Separators can come in the form of disks, rods, glass beads, and woven fabrics. Dunk-type batteries may utilize a nonwoven, absorbent, nonconductive material to both separate the electrodes and absorb the electrolyte. Further, the battery 12 may include a wicking material between one or more of the anode, the cathode, and/or the separators. The wicking material may enhance the ability of the battery 12 to activate upon exposure of water by directing the water to areas of the battery 12 that trigger the chemical reaction, such that the electrical voltage may be generated and supplied to the electrical circuit 14 and/or the memory 16.

In some embodiments, the battery 12 may include one or more cells that each include the cathode, the anode, and/or the separators. For example, the battery may include four cells that are spaced apart from one another at a predetermined distance. In other embodiments, the battery 12 may include less than four cells (e.g., three, two, or one cell) or more than four cells (e.g., five, six, seven, eight, nine, ten, or more cells). Further, in some cases, an efficiency of the battery 12 may be based on the spacing between the cells. For example, cells of the battery 12 may release heat and/or chemicals that may affect the operation of other cells in the battery 12. Accordingly, spacing the cells at a distance that reduces an amount of heat transferred between cells, but also reduces a size of the battery 12 may be predetermined to maximize an efficiency of the battery 12. In some embodiments, the cells of the battery 12 may include various materials, which may also effect an efficiency of the battery 12. For example, the cells of the battery 12 may include magnesium oxide, carbon acetate, copper, and/or another suitable material that may be configured to generate an electrical voltage upon exposure to water. In some cases, water may trigger a chemical reaction in the cells of the battery 12, which may cause a circuit in the battery 12 to close, thereby enabling electrical voltage to flow to an outlet (e.g., a portion electrically coupled to the electronic circuit 14 and/or the memory 16) of the battery 12. In certain embodiments, the battery may be activated when exposed to between 0.1 milliliters (mL) and 5 mL of water, between 0.5 mL and 3 mL of water, between 1 mL and 2 mL of water, or approximately (e.g., within 5% of or within 10% of) 1.5 mL of water.

In some embodiments, the water detection device 10 may include an additional battery 32 (e.g., a test battery) that may be separate from the battery 12. The additional battery 32 may not be water-activated and may be continuously in an active condition (e.g., configured to provide an electrical voltage). The additional battery 32 may then be used to test a condition of the electronic circuit 14 and/or the memory 16 by supplying the electrical voltage to the electronic circuit 14 and/or the memory 16 and determining whether such components are operating properly. In some embodiments, the additional battery 32 may enable the electronic circuit 14 to provide intermittent signals to the electronic device 30. For example, the additional battery 32 may periodically provide an electrical voltage to the electronic circuit 14, such that the electronic circuit 14 may perform a self-diagnosis and communicate with the electronic device 30 and/or the network 22. When the battery 12 activates (e.g., water contacts the battery 12), the electronic circuit may then provide a continuous signal and/or communication with the electronic device 30 and/or the network 22. For example, the intermittent signals may become so frequent that the signal and/or communication seems continuous or the continuous signal may override/overlay the intermittent signals. In still further embodiments, the additional battery 32 may be configured to receive electrical charge wirelessly through a radio frequency (RF) device (e.g., an interrogator device that emits an electrical field toward an indicator to detect a characteristic of a component). For example, the electronic circuit 14 may be associated with an RF tag that may provide the RF device with information associated with the electronic circuit 14 (e.g., a status of the electronic circuit, a condition of the electronic circuit, and/or a function in which the electronic circuit performs). Thus, when the RF device emits the electrical field, the additional battery may absorb electrical energy and charge itself.

Further, the water detection device 10 may include a temperature sensor 34 and/or a chemical sensor 36. In some embodiments, the temperature sensor 34 may also be utilized to determine a presence of water. For example, the temperature in the environment surrounding the water detection device 10 may rapidly decrease upon exposure to a significant amount of water. Thus, the temperature sensor 34 may provide a confirmation that the water detection device 10 is operating properly. Additionally, the chemical sensor 36 may be utilized to monitor characteristics of the water when the water detection device 10 is exposed to water. In some cases, it may be desirable to determine whether any contaminants are present in the water upon detection of the water. For example, the water detection device 10 may be located in the interior of a structure that stores chemicals. Upon a flood event, it may be desirable to determine what chemicals may be present within the water to determine what procedures, if any, should be followed to subsequently eliminate such chemicals.

While the battery 12, the temperature sensor 34, and/or the chemical sensor 36 may be exposed to water upon a water detection event, the electronic circuit 14 and/or the memory 16 may be included in a separate housing (e.g., beacon) that seals such components from the water and/or other substances. As such, when the water enters the housing of the water detection device 10, the battery 12 may generate the electrical voltage that supplies power to the electronic circuit 14 and/or the memory 16, but the water may be blocked from contacting the electronic circuit 14 and/or the memory 16. Therefore, the electronic circuit 14 and/or the memory 16 may be utilized for multiple water detection events without degrading and/or otherwise incurring damage. However, the battery 12 may be replaced upon each water detection event. As discussed above, the battery 12 may be modular with respect to a housing of the water detection device 10 to facilitate replacement of the battery 12 with a new battery 12 that may be dormant until exposed to water.

While a single water detection device 10 is shown in FIG. 1, it should be noted that more than one of the water detection devices 10 may be used together (e.g., one, two, three, four, five, six, seven, eight, nine, ten, or more of the water detection devices 10 may be connected to the same electronic network 22 and/or electronic device 30). In such embodiments, a location of each of the water detection devices 10 may be recorded to correspond to a device number of a corresponding water detection device 10. Such information may be recorded in a table for presentation via a graphical user interface (GUI) (see e.g., FIG. 13) of a software program and/or another suitable location (e.g., memory associated with the electronic network 22). To further assist the user to determine a location of one of the water detection devices 10, the location of the water detection devices 10 may be displayed in a GUI with reference to a floor plan, map, or schematic representation of the structure in which the water detection devices are deployed, as shown in FIG. 14.

As discussed above, the electronic device 30 may communicate with the water detection device 10. In some embodiments, the electronic device 30 may include software that may be utilized directly with the water detection device 10. For example, the electronic device 30 may include an application or computer program that may be configured to recognize and/or interact with the water detection device.

In some embodiments, the electronic circuit 14 may be capable of transmitting a wireless electronic signal for communication with the electronic network 22 using one or more of a variety of wireless communication techniques. For example, the electronic circuit 14 may be configured to wirelessly communicate with the electronic network 22 using Wi-Fi, near field communication, Bluetooth, Zigbee, Z-wave, ISM, an embedded wireless module, or another suitable wireless communication network. Further, the electronic circuit 14 may be programmed to send a message to an address via the electronic network, such as an IP address, URL, email address, telephone number, a dedicated monitoring station, or other type of electronic address known to those of skill in the art, and any combination of the same. The message that may be sent to the user is described in detail herein with reference to FIGS. 10-14.

In some embodiments, the memory 16 of the water detection device 10 may be capable of wireless communication 62 with an interrogator 60 (e.g., the RF device) for inputting into the memory 16 information such as a physical location of the water detection device 10. In some embodiments, the memory 16 may include a radio-frequency identification (RFID) circuit. RFID circuits may be passive, active, or battery-assisted passive. As used herein, an active circuit includes an on-board battery and periodically transmits an ID signal, a battery-assisted passive circuit has a small battery on board (e.g., the battery 32) and is activated when in the presence of an RFID reader such as the interrogator 60, and a passive RFID circuit is powered by the radio energy transmitted by the interrogator 60 alone. In some embodiments, the RFID circuit may be read-only, such that the memory 16 includes a factory-assigned serial number that is used as a key to a database (e.g., a database that includes location information of one or more water detection devices 10). In other embodiments, the RFID circuit may be read/write, where the water detection device 10 and physical location information may be written into the memory 16 using the interrogator 60.

Figure 2:
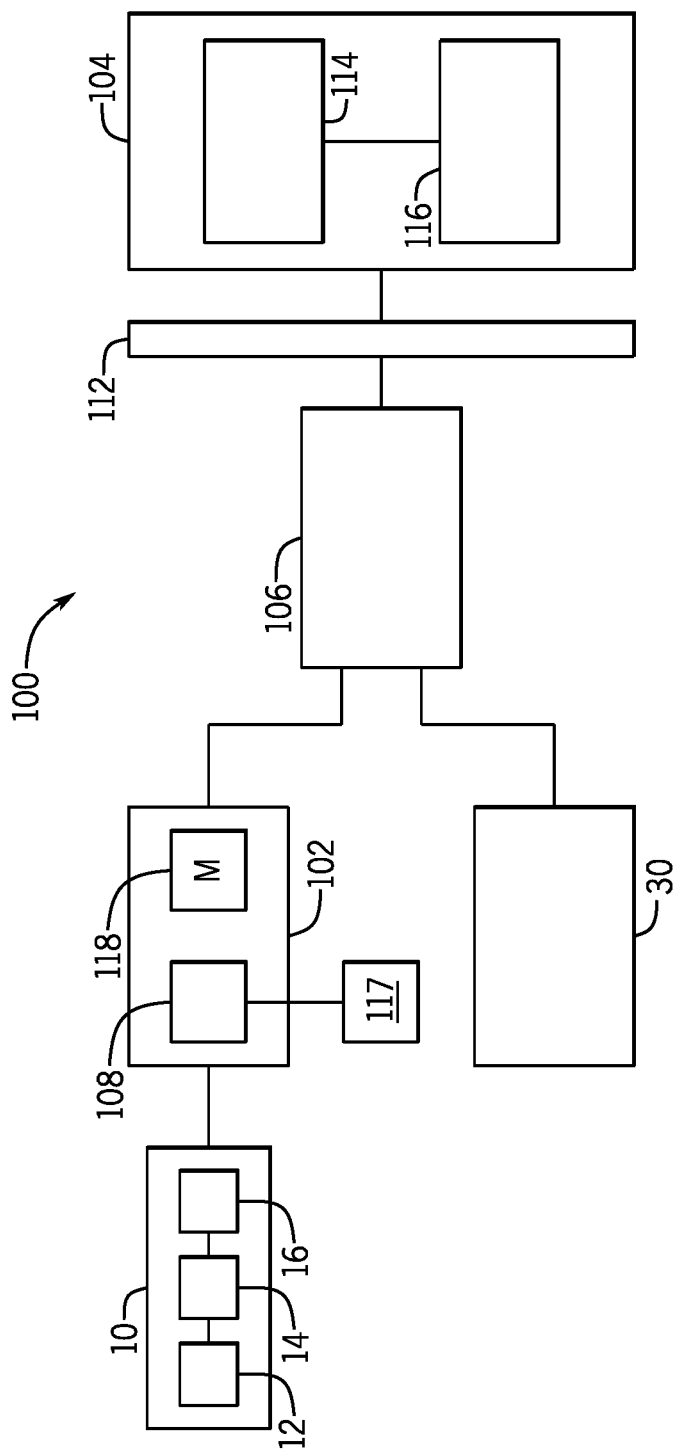
FIG. 2 is a schematic of an embodiment of an overall network that the water detection device of FIG. 1 may utilize to communicate with various electronic devices, in accordance with an aspect of the present disclosure.

FIG. 2 is a schematic view of a bridge 100 for electronically coupling a hub 102 for the water detection device 10 to a remotely located monitoring entity 104 through a suitable network such as the Internet 106. In some embodiments, the hub 102 is positioned in a structure (e.g., a building or a residential home) that includes a plurality of the water detection sensors 10. Each of the water detection sensors 10 may be configured to communicate with the hub 102 through a wireless connection, such as Wi-Fi, near field communication, Bluetooth, Zigbee, Z-wave, ISM, an embedded wireless module, or another suitable wireless communication network. The hub 102 may continuously monitor the status of each of the water detection sensors 10 and report the status to the monitoring entity 104. The hub 102 may have a display 108 to indicate the status of the hub 102, such as one or more light emitting diodes (LEDs) (e.g., one LED may flash red to indicate that the hub 102 is working properly, one LED to flash green when a script is scanning, and one LED to flash yellow when the hub 102 is posting).

The user of the water detection system 10 may then control and monitor the system with the electronic device 30 (e.g., a smartphone, a computer, a tablet, and/or another suitable electronic device coupled to the hub 102, such as through a wireless connection). The monitoring entity 104 may include a firewall 112, a server 114, and a database 116 for storing detection event reports. Other visual indicators 117 may be included such as electrically conductive wall paint that emits light and/or changes color when one of the water detection sensors 10 is activated. In still further embodiments, the hub 102 may be configured to send a message (e.g., a text message) to the user via the electronic device 30. As discussed in detail below, the message may include a photographic image of a location of the respective water detection device 10 reporting the detection event. For example, when installing the water detection devices 10, the user (or another installer) may photograph and store images of each water detection device 10 positioned in its respective location to provide a visual cue as to which water detection device 10 detects the detection event. Further, a location of each of the water detection sensors 10 may be identified by the user and/or otherwise stored in memory 118 of the hub 102 for later provision upon detection of water (e.g., a threshold level of moisture).

In some embodiments, the monitoring entity 104 may be the interrogator 60, which may be utilized to test a condition of the water detection device 10. For example, the interrogator 60 (e.g., an RFID reader) may supply electrical power to a test battery (e.g., an RFID passive circuit) of the water detection device 10, which may then activate the electronic circuit 14 and/or the memory 16, such that the electronic circuit 14 and/or the memory 16 may communicate with the interrogator 60. The communication between the electronic circuit 14 and/or the memory 16 and the interrogator 60 may be indicative of the condition of the water detection device 10. As discussed above, the electronic circuit 14 may communicate with the network 22, the electronic device 30, and/or the interrogator 60 intermittently before activation of the battery 12 (e.g., when a test is activated or engaged). When the battery 12 is in an active condition, the communications between the electronic circuit 14 and the network 22, the electronic device 30, and/or the interrogator 60 may become continuous (or appear substantially continuous).

Figure 3:
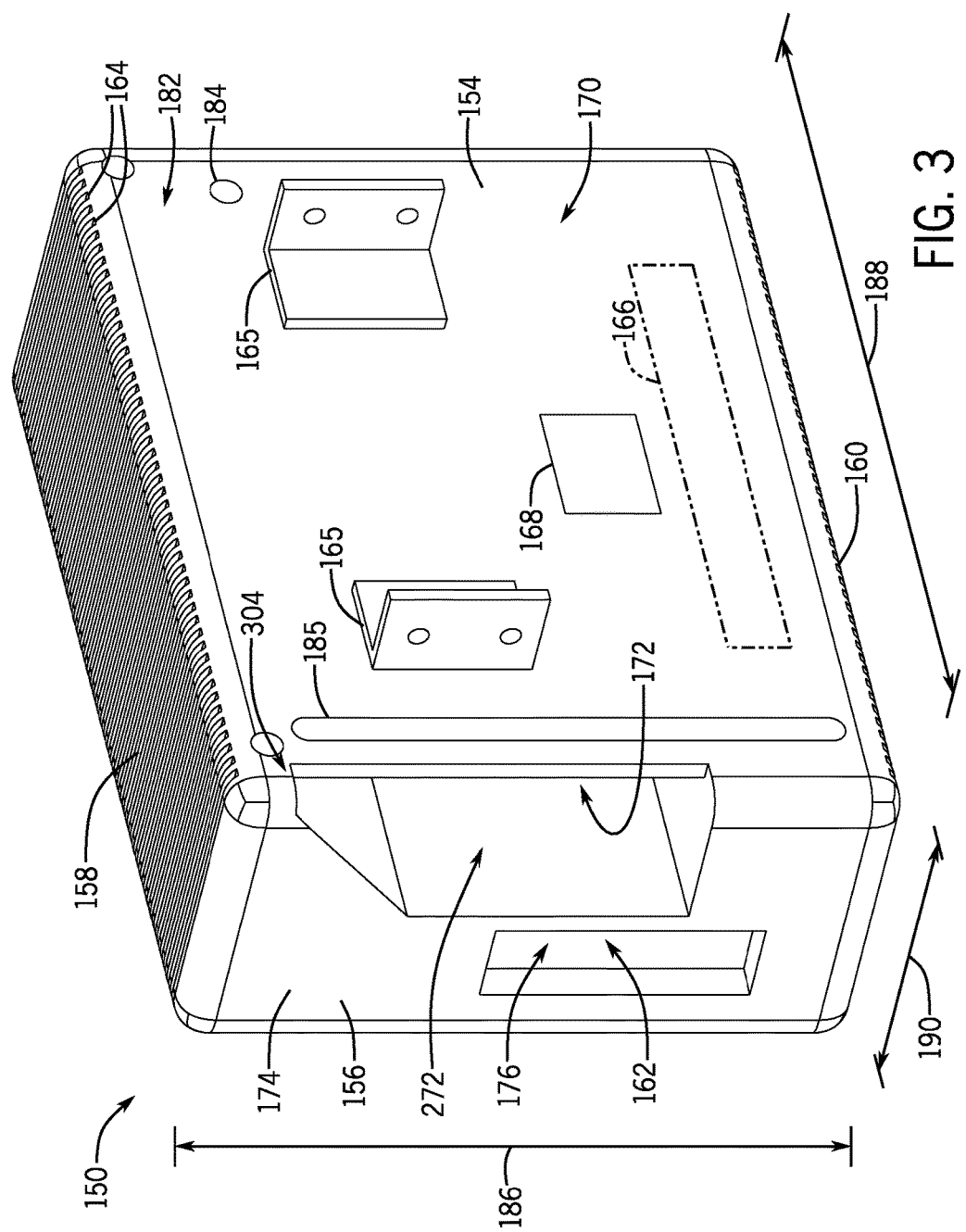
FIG. 3 is a perspective view of an embodiment of a housing that forms and may receive one or more components of the water detection device of FIG. 1, in accordance with an aspect of the present disclosure.

FIGS. 3-9 are perspective views of embodiments of a housing 150 of the water detection device 10 and/or a component housing 152 that may include the electronic circuit 14 and/or the memory 16 (e.g., a communication beacon). The housing 150 may receive the component housing 152, and include features that may couple the battery 12 to the electronic circuit 14 and/or the memory 16. For example, FIG. 3 is a perspective view of an embodiment of the housing 150 for the water detection device 10 having a generally rectangular shape (e.g., rectangular cross-section) with opposed sidewall s 154, opposed end walls 156, a top wall 158 and a bottom wall 160 defining a chamber 162 therein. In the illustrated embodiment, the top and bottom walls 158 and 160 include a plurality of fluid passageways 164 (e.g., capillaries) that are configured to draw liquid into the chamber 162 through capillary action. In other embodiments, more or different walls may include the fluid passageways 164 (e.g., capillaries). The fluid passageways 164 are described in detail below with reference to FIG. 5. While the illustrated embodiment of FIG. 3 shows the housing 150 having a rectangular shape, it should be recognized that the housing 150 may be any suitable shape, such as cube-shaped or substantially spherical. In some cases, the shape of each of the water detection devices 10 may depend on a location in which a respective water detection device 10 will be placed. For example, a water detection device 10 that is positioned behind a wall may be generally rectangular, as shown in FIG. 3, while a water detection device 10 positioned underneath a sink may be cube-shaped, spherical, and/or another suitable shape. Further, a water detection device 10 disposed in a corner may be prismatic.

The water detection device 10 may include one or more members 165 or mechanisms for attaching the water detection device 10 to a structure such as a pipe, valve, wall, fixture, or other mounting component. The one or more members 165 may enable the water detection device 10 to be secured in a specific location and detect water that may accumulate in the specific location in a relatively short time period. In other words, the one or more members 165 may secure the water detection device 10 to the mounting component and position the water detection device 10, such that the water detection device 10 may receive water when a leak or another water exposure event first occurs. In some embodiments, the members 165 are rounded and/or configured to conform to a mounting component, which facilitates positioning in certain locations (e.g., attaching the water detection device 10 to a low point of a drain pipe).

In some embodiments, a conductive material 166 may extend as a sheet along the sidewalls 154 and is connected to the electronic circuit 14 of the water detection device 10. Such a configuration may enable the electronic circuit 14 to be programmed from outside of the housing 150 (e.g., information related to the message, desired address, device number, and physical location information may be programmed into the memory 16). In other embodiments, the housing 150 may include pins as the conductive material 166 that protrude from the sidewalls 154 to enable the electronic circuit 14 to be programmed without removing the electronic circuit 14 and/or otherwise disassembling the water detection device 10. For example, a seal (e.g., a silicone seal) may be formed at openings in the housing 150 from which the pins protrude. In still further embodiments, the conducting material 166 may not be included and the electronic circuit 14 may be programmed before being inserted into the housing. In some embodiments, the housing 150 may be labeled or include an indicator 168 (e.g., a QR code or an RFID circuit) on a surface 170 of the housing 150 to enable the identity of the housing 150 to be determined by scanning the indicator. In other embodiments, the indicator 168 may be positioned on another suitable surface of the housing 150. In still further embodiments, the indicator 168 may not be included. The indicator 168 may be detected by the interrogator 60, which may then communicate the identity of the housing 150 to the electronic device 30, for example.

As shown in the illustrated embodiment of FIG. 3, the housing 150 may be modular in that the housing 150 has an opening 172 in a rear wall 174 (or another wall in other embodiments) that is configured to receive the component housing 152, which may include the electronic circuit 14 (e.g., Bluetooth communication circuitry). In some embodiments, the component housing 152 is configured to slide into the opening 172 of the housing 150. Sliding the component housing 152 into the opening 172 may reduce friction, torque, and/or other stress on leads and/or other features that may be included on or within the component housing 152. Further, sliding the component housing 152 into the opening 182 may align the component housing 152, such that a connection between the component housing 152 and the battery 12 is facilitated. In other embodiments, the opening 172 includes an interference fit that enables that component housing 152 to snap into the opening 172 and secure the component housing 152 within the opening 172. In such embodiments, a tool may be utilized to disconnect and/or remove the component housing 152 from the opening 172.

Figure 4:
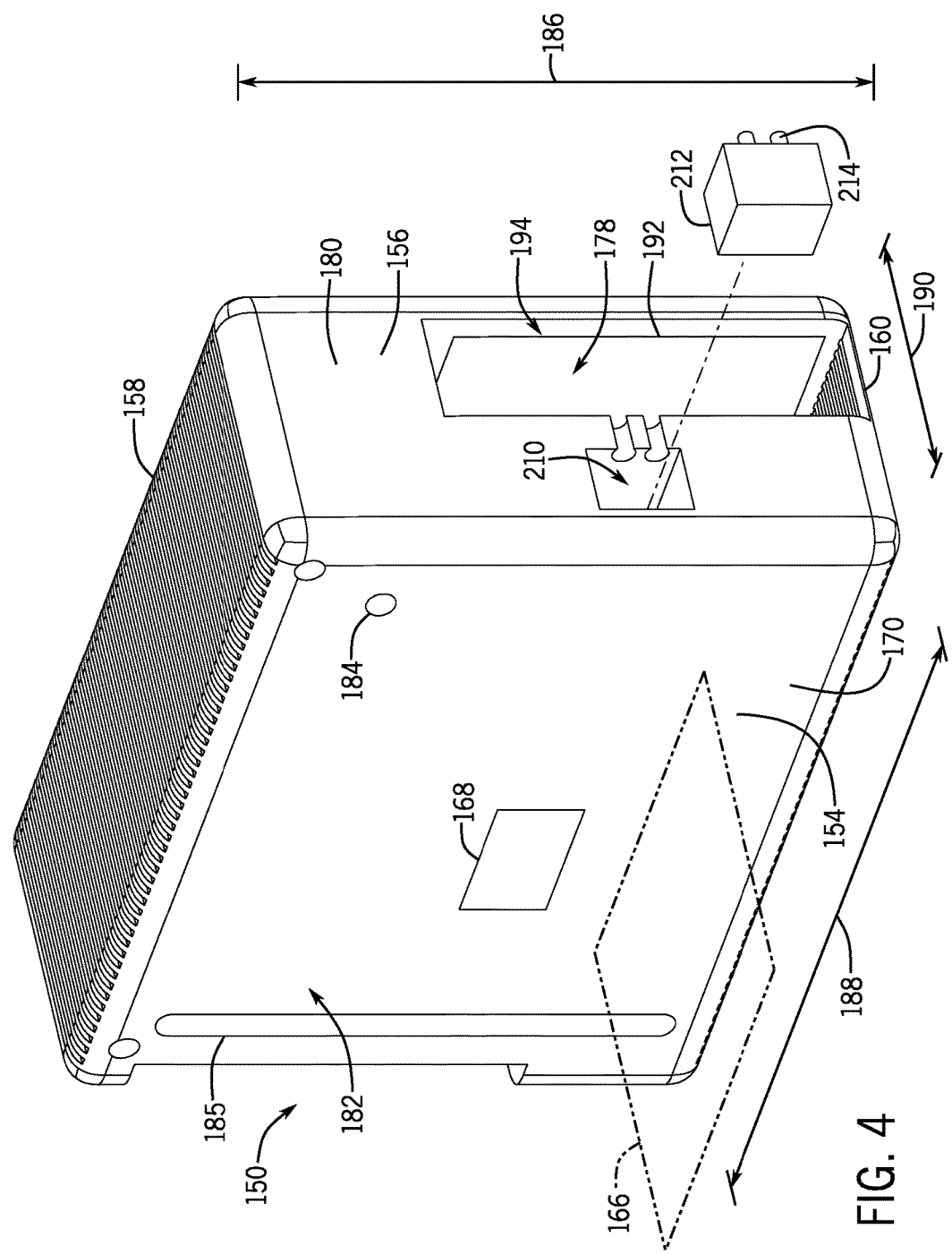
FIG. 4 is a perspective view of an embodiment of the housing of FIG. 3 that forms and may receive one or more components of the water detection device of FIG. 1, in accordance with an aspect of the present disclosure.

In any case, the component housing 152 may be removed from the opening 172 and used with another housing 150 after the housing 150 has been damaged by use, for example. Also, different component housings 152 may be used to provide varied functions, such that the component housing 152 may be replaced with another component housing 152 that performs a desired function (e.g., smoke detection) and/or transfers signals via different techniques (e.g., radio-frequency identification technology, Wi-Fi, Bluetooth, near field communication, Zigbee, or another suitable wireless communication technique). Additionally, the housing 150 may include a second opening 176 (e.g., the chamber 162) that may be configured to receive the battery 12 and/or another component of the water detection device 10. In some embodiments, the second opening 176 may facilitate removal of the battery 12 from the housing 150. For example, the user may apply a force on the battery 12 through the second opening 176 to direct the battery 12 out of the housing 150 via a third opening 178 (e.g., in a front wall 180), as shown in FIG. 4. The third opening 178 may be larger in size than the second opening 176, such that the battery 12 may not be removed from the housing 150 through the second opening 176. However, in other embodiments, the second opening 176 and the third opening 178 may be approximately (e.g., within 5% or within 10%) the same size. As shown in the illustrated embodiment of FIG. 3, the opening 172 and the second opening 176 may be isolated from one another, such that water that enters the housing 150 via the second opening 172 is blocked from contacting components in the opening 172. In other embodiments, the opening 172 and the second opening 176 may not be isolated from one another, but the component housing 152 may include a substantially water-tight seal (e.g., a silicone based seal) to block water from contacting the electronic circuit 14 and/or the memory 16.

As discussed above, to increase the shelf life of the battery 12, the housing 150 may be coated with a water-soluble coating 182 to seal the chamber 162 from the external environment. When a sufficient amount of water contacts the coating 182, the coating may dissolve, thereby enabling water to enter the housing 150 through the fluid passageways 164 and activate the battery 12. That is, the coating 182 may block access to the fluid passageways 164 to limit potential for small quantities of water (e.g., mere humidity) to activate the battery 12. Accordingly, the battery 12 may supply power to the electronic circuit 14, which may in turn, send a message that advises a user about a detection event (e.g., a leak detection event). In some embodiments, the coating 182 may be disposed between the fluid passageways 164, such that water dissolves the coating 182 before the water may enter into the housing 150. Additionally or alternatively, the housing 150 may have a multiple-layer sidewall that includes a water porous material covered by the water-soluble coating 182. The water-soluble coating 182 may be applied to the substrate material by any suitable means such as dipping, spraying, brushing, 3D printing, or another suitable technique. In some embodiments, the water-soluble coating 182 may include sugar glass, water-soluble polymers (e.g., polyvinyl alcohol, polyvinyl pyrrolidone, sorbitol, etc.), a combination thereof, or any other suitable material.

In any case, the coating 182 may protect the battery 12 from exposure to humidity and/or other contaminants. For example, humidity and/or contaminants may degrade, damage, or cause improper activation of the battery 12. Accordingly, the coating 182 may block humid air and/or contaminants from entering the housing 150 before a sufficient amount of water is exposed to the water detection device 10 to dissolve or otherwise remove the coating 182. In some embodiments, a thickness of the coating 182 may be varied depending on a location or function of the water detection device 10. For example, a thickness of the coating 182 may be increased when the water detection device 10 is configured to determine a flood event or when positioned in a humid climate and decreased when the water detection device 10 is configured to detect a leak (e.g., less water may dissolve the coating 182).

In certain embodiments, the housing 150 may include a visual indicator 184, such as a light emitting diode (LED), and/or an audio indicator that may alert a user of a detection event. Therefore, the user may be alerted by both the electronic device as well as the visual indicator 184 and/or the audio indicator on the housing 150. Further still, the housing 150 may include a level indicator 185 that may be utilized to enable the user to determine a severity of the detection event. For instance, the level indicator 185 may indicate how much water was present within the water detection device 10. In some embodiments, the level indicator 185 may include a water activated coating (e.g., paint) on an inner surface of the housing or another suitable device that may be utilized to provide an indication of an amount of water that collects within the housing (e.g., a window that enables the user to view the chamber 162 of the housing 150.

Further, the housing 150 may include air pockets that may enable the water detection device 10 to float or otherwise increase in buoyancy when exposed to a level of water that exceeds a position of the air pockets within the housing 150 with respect to a height 186, a length 188, and/or a width 190 of the housing 150, depending on orientation. The air pockets within the housing 150 may facilitate retrieval of the water detection device 10 when a large amount of water is present (e.g., a flood) because the water detection device 10 may be visible above a surface defined by the water. In some embodiments, the air pockets may include sealed pouches of air. In other embodiments, the air pockets may include compartments within the housing 150 that are filled with air and then sealed using a sealing technique (e.g., welding, silicone based seals, etc.).

The housing 150 of the water detection device 10 may also include compression components 192 to enhance performance of the water detection device 10. For example, the compression components 192 may be disposed in the second opening 176 (and/or the third opening 178) and may include a resilient material (e.g., a flexible material) that may provide compression against the battery 12 when the battery 12 is disposed in the second opening 176 (and/or the third opening 178). In some cases, the battery 12 may expand when exposed to water, and thus, the compression components 192 may be configured to enable the battery 12 to expand within the second opening 176 (and/or the third opening 178) without applying a significant force against the housing 150 while also resisting the expansion and increasing battery efficiency. In some embodiments, the compression components 192 may include a material such as polylactic acid (PLA), acrylonitrile butadiene styrene (ABS), another suitable resilient material, or a combination thereof. In any event, the compression components 192 may provide a tolerance between the battery 12 and a wall 194 of the housing 150 to accommodate any expansion of the battery 12. In some embodiments, the tolerance may be between 0.01 millimeter (mm) and 1 mm, between 0.1 and 0.5 mm, between 0.2 and 0.4 mm, or approximately (e.g., within 5% or within 10% of) 0.4 mm.

FIG. 4 is a perspective view of another embodiment of the housing 150 that shows the third opening 178 as well as a fourth opening 210. As discussed above, the third opening 178 may receive the battery 12, such that the battery 12 is inserted into and removed from the housing 150 via the third opening 178. The fourth opening 210 may be configured to receive an intermediate connector 212 that may be utilized to establish an electrical connection between the battery 12 and the electronic circuit 14 and/or the memory 16. For example, the intermediate connector 212 may include one or more contact points 214 (e.g., pins and/or another electrically conductive member) that may establish an electrical pathway between the battery 12 and the electronic circuit 14 and/or the memory 16. The intermediate connector 212 may establish the electrical connection between the battery 12 and the electronic circuit 14 and/or the memory 16 to further isolate the electronic circuit 14 and/or the memory 16 from the chamber 162, and thus from water that may enter the housing 150. For example, in some embodiments, the intermediate connector 212 may be disposed in the fourth opening 210 after the battery 12, the electronic circuit 14, and/or the memory 16 are disposed in the housing 150. In any event, the intermediate connector 212 may further isolate the electronic circuit 14 and/or the memory 16 from contact with water. Additionally, the intermediate connector 212 may facilitate removal of the electronic circuit 14 and/or the memory 16 from the housing 150 (e.g., the intermediate connector 212 may be disconnected and the component housing 152 removed).

Figure 5:
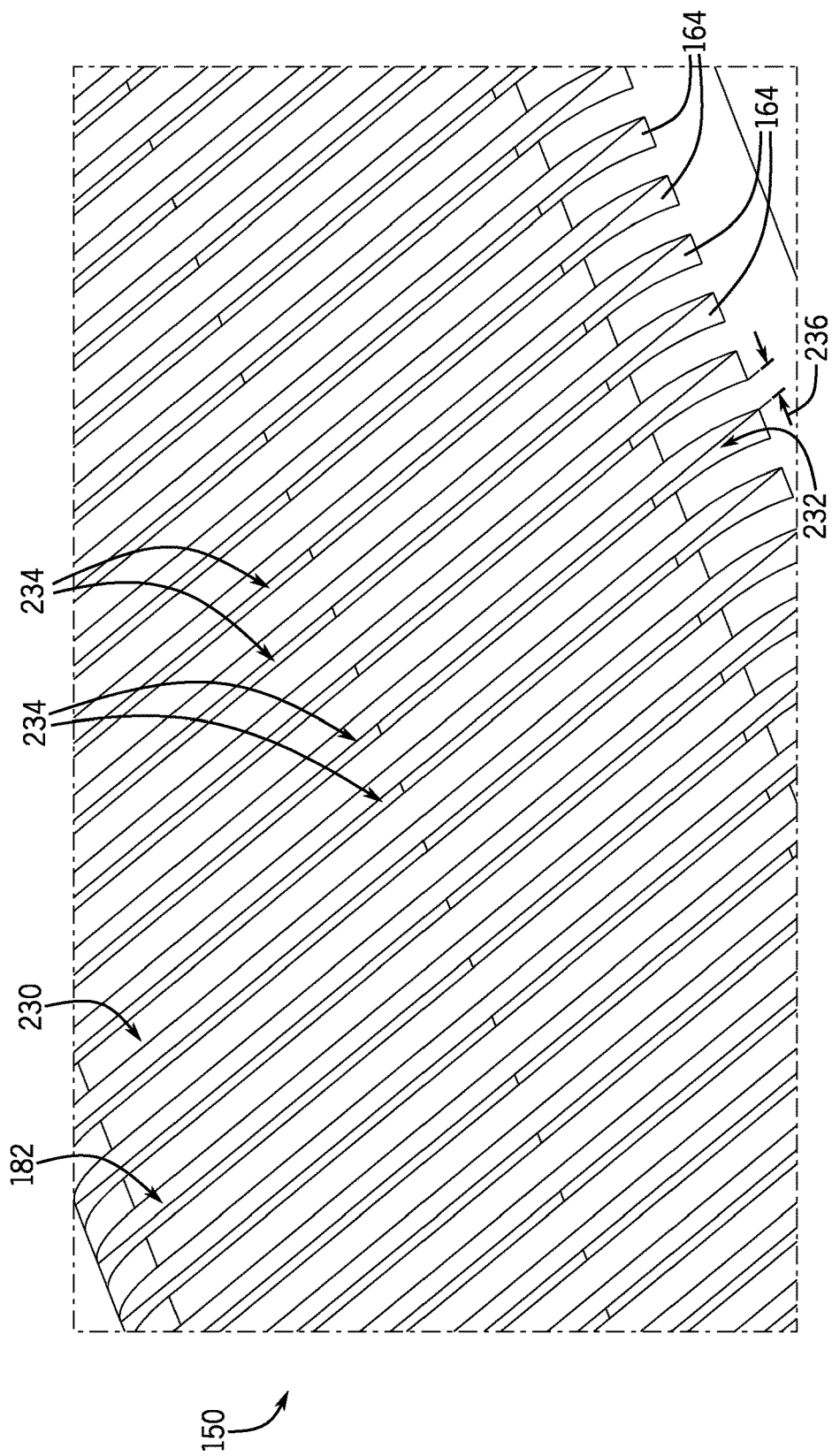
FIG. 5 is an expanded, perspective view of fluid passageways that may be included on an outer surface of the housing of FIGS. 3 and 4, in accordance with an aspect of the present disclosure.

As discussed above, the housing 150 may include the fluid passageways 164 (e.g., capillaries) that may direct water to flow into the housing 150 toward the battery 12. For example, FIG. 5 is an expanded, perspective view of an embodiment of the fluid passageways 164 that may be included on a surface 230 of the housing 150. The fluid passageways 164 may include channels 232 that include openings 234. The openings 234 may be disposed above the battery 12, such that water flowing through the channels 232 and into the openings 234 may contact the battery 12. In some embodiments, water may be directed through the passageways 164 into the housing 150 and toward the battery 12 through adhesion (e.g., attraction of water molecules to the surface 230, the fluid passageways 164, and/or ambient air), cohesion (e.g., attraction of water molecules to one another), and/or surface tension (e.g., ability of the water molecules to form a film or droplets due to the cohesion forces being stronger than the adhesion forces). The forces of adhesion, cohesion, and/or surface tension may enable water to flow through the channels 232 of the passageways 164 and ultimately drop into the housing 150 through the openings 234.

In some embodiments, the passageways 164 may enable a relatively small amount of water coming into contact with the housing 150 to activate the battery 12 because substantially all (e.g., above 90%, above 95%, or above 98%) water that contacts the housing 150 may be directed into the openings 234 via the channels 232 to ultimately contact the battery 12. Thus, the water detection device 10 may be configured to detect leaks that are relatively minor (e.g., produce a low flow rate of water). As discussed above, in some embodiments, the housing 150 may include the coating 182 that may block contaminants and/or humidity from entering the housing 150. However, when a certain amount of water contacts the housing 150, the coating 182 may dissolve, thereby enabling the water to enter the housing 150 through the openings 234 and ultimately contact the battery 12.

As shown in the illustrated embodiment of FIG. 5, the passageways 164 may be spaced a distance 236 from one another. In some embodiments, the distance 236 may be uniform throughout the length 188 of the housing 150. In other embodiments, the distances 236 between each of the passageways 164 may be non-uniform. The distance 236 between each of the passageways 164 may be between 0.01 centimeters (cm) and 1 cm, between 0.05 cm and 0.75 cm, between 0.1 cm and 0.6 cm, or between 0.3 cm and 0.5 cm. In any event, the distance 236 may enable the water to be directed from the surface 230 of the housing 150 into the housing 150 via the passageways 164 (e.g., via capillary action). While the illustrated embodiment of FIGS. 3 and 4 shows the passageways 164 as being positioned on a top 238 and a bottom 240 of the housing 150, in other embodiments, the passageways 164 may be positioned on another suitable surface of the housing or at least a portion of all external surfaces. In any case, the housing 150 may be mounted, such that the passageways 164 may be exposed to water relatively early in the event of a leak and/or detection event, such that the water may activate the battery 12 as quickly as possible when a detection event occurs.

FIGS. 6-9 show embodiments of the component housing 152 that may be used to receive the electronic circuit 14 and/or the memory 16. As shown in the illustrated embodiment of FIG. 6, the component housing 152 which includes a socket 260 for electrically coupling the electronic circuit 14 to the battery 12. For example, the socket 260 may be an opening that is configured to receive the intermediate connector 212 to provide the electrical pathway between the battery 12 and the electronic circuit 14 and/or the memory 16 while also further isolating the electronic circuit 14 and/or the memory from the chamber 162 in which water may enter the housing 150. Further, the component housing 152 may include an opening 262 that may enable a pair of antennae 266 of a signal enhancing module 267 received in the opening 262 to protrude from the component housing 152. In some embodiments, the antennae 266 may be coupled to the electronic circuit 14 and may be configured to wirelessly communicate with the electronic device 30, the hub 102, and/or another suitable device. In other embodiments, the opening 262 may be configured to receive physical connectors that are coupled to the electronic circuit 14, such that the electronic circuit 14 may be electrically coupled to the electronic device 30, the hub 102, and/or another suitable device by a hardwire connection.

Additionally, the component housing 152 may include a recess 268 that may be configured to receive the electronic circuit 14 and/or the memory 16. In some embodiments, the electronic circuit 14 and/or the memory 16 may be disposed in the recess 268 and the recess 268 may then be sealed (e.g., via a silicone seal), such that water and/or other contaminants are blocked from contacting the electronic circuit 14 and/or the memory 16. Further, the intermediate connector 212 may be sealed in the socket 260 (e.g., a silicone seal) and/or the antennae 266 may be sealed in the opening 262 (e.g., a silicone seal) to enhance the seal of the component housing 152 and block water and/or other contaminants from contacting the electronic circuit 14 and/or the memory 16.

Figure 6:
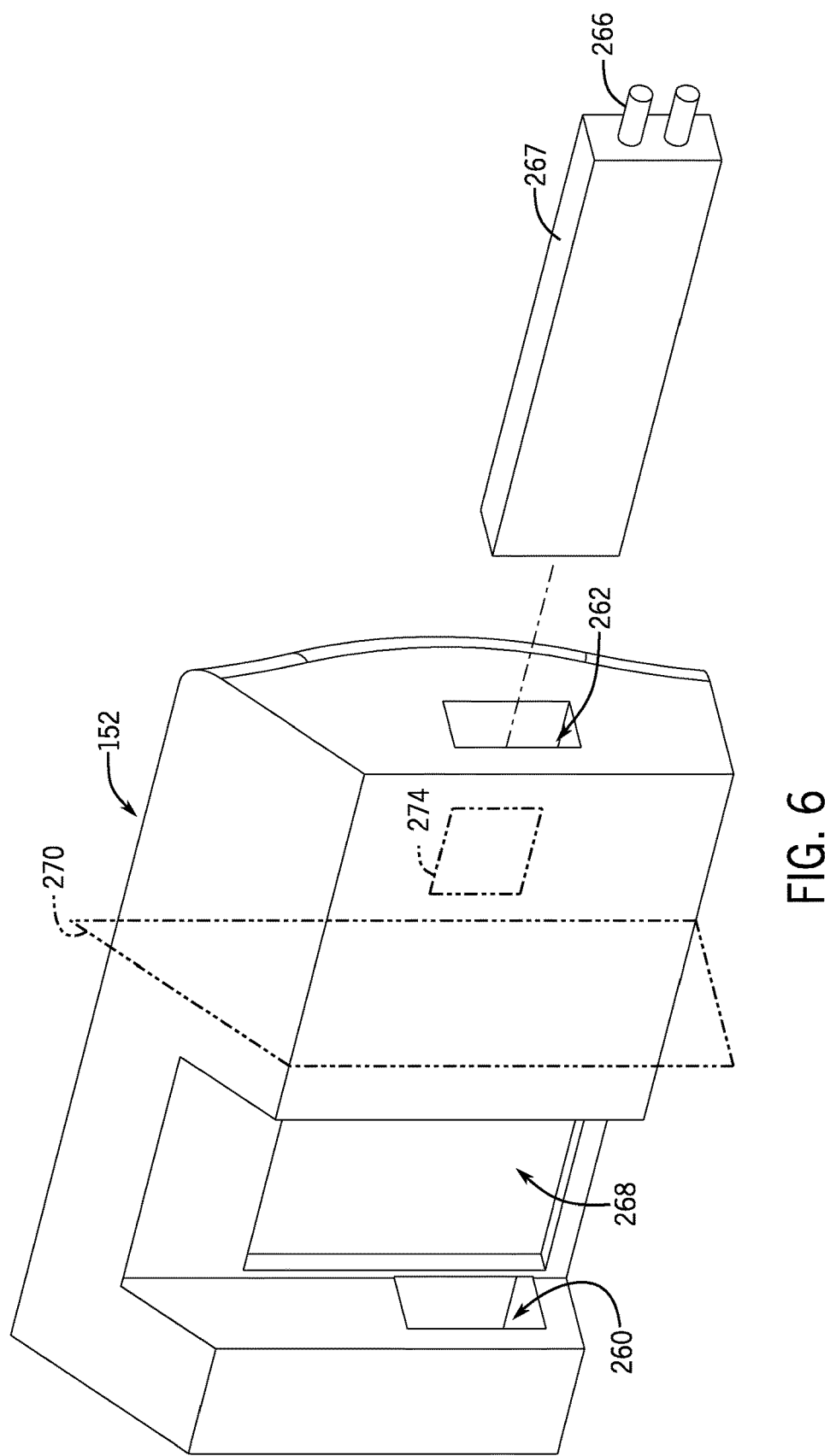
FIG. 6 is a perspective view of an embodiment of a component housing that may be configured to be disposed within the housing of FIGS. 3 and 4, in accordance with an aspect of the present disclosure.

As shown in the illustrated embodiment of FIG. 6, the component housing 152 may include a cross-sectional shape (e.g., when taken along a plane 270) that substantially conforms to a shape of the opening 172 of the housing 150 of the water detection device 10. Accordingly, in some embodiments, the component housing 152 may be disposed in the opening 172 of the housing 150, and then sealed to block water and other contaminants from entering a chamber 272 formed by the opening 172 (see, e.g., FIG. 3). Further, the shape may establish a poka-yoke assembly between the opening 172 and the housing 152.

In any case, the component housing 152 may be removed from the housing 150, such that the water detection device 10 is modular. In some cases, it may be desirable to utilize different wireless communication techniques to provide information from the water detection device 10 to the electronic device 30, or vice versa. Accordingly, the component housing 152 may be removed and replaced with another component housing 152 that includes an electronic circuit 14 configured to utilize the desired wireless communication technique. In certain embodiments, the component housing 152 may be removed from the housing 150 to program the electronic circuit 14. While the illustrated embodiment of FIG. 6 shows the component housing 152 having the antennae 266, in other embodiments, the electronic circuit 14 may not include the antennae 266 and/or physical connectors that extend through the opening 262, but the electronic circuit 14 may still be programmed without being removed from the housing 150 (e.g., via the conductive strip 166). In still further embodiments, the component housing 152 may be removed to program the electronic circuit 14. Additionally, the component housing 152 may be removed from the housing 150 in order to replace the component housing 152 with another component housing 152 that includes an electronic circuit 14 that may be configured to perform another function other than water detection (e.g., gas detection, smoke detection, acetone detection, and/or another suitable function). Thus, the component housing 152 that may be disposed in the housing 150 may be chosen based on the desired function that is to be performed. The housing 150 may then be placed in a suitable location to perform the desired function (e.g., water detection).

Additionally, the component housing 152 may include an indicator 274 (e.g., a QR code) on an outer surface 276 of the component housing 152. The indicator 274 may associate the component housing 152 with the electronic circuit 14, which may be configured to perform predetermined functions (e.g., the indicator 274 may be coupled to the electronic circuit 14). In some embodiments, the indicator 274 may be detected (e.g., scanned) by the interrogator 60. Accordingly, the indicator 274 may provide information related to the electronic circuit 14 (e.g., a condition, a status, a function in which the electronic circuit performs, or a combination thereof) to the interrogator 60. The interrogator 60 may then communicate information related to the electronic circuit 14 and/or the component housing 152 to the electronic device 30, for example. Further, the electronic device 30 may be configured to associate information related to the housing 150 with the information related to the electronic circuit 14 and/or the component housing 152. For example, the housing 150 may be associated with a position within a structure (e.g., a home or other building), such that the function of the electronic circuit 14 and/or other information of the electronic circuit 14 may be linked to the location of the housing 150.

In some embodiments, the component housing 152 may include components that may enable the condition of the electronic circuit 14 to be tested without removing the component housing 152 from the housing 150. For example, the component housing 152 may include the additional battery 32 (not shown) that may be coupled to the electronic circuit 14 and configured to provide power to the electronic circuit 14 upon activation of a test. Therefore, the electronic circuit 14 may communicate with the network 22, the electronic device 30, and/or the interrogator intermittently (e.g., when a test is activated and/or engaged to provide power to the electronic circuit). Additionally or alternatively, the additional battery 32 may constantly supply power to the electronic circuit 14, such that the electronic circuit 14 may continuously send and receive signals to and from the electronic device (e.g., directly and/or through the interrogator 60). In certain embodiments, a test may be activated using the interrogator 60, which may communicate with the indicator 274 of the component housing 152 and/or the electronic circuit 14 directly. In other embodiments, the component housing 152 may not include the additional battery. In such embodiments, power may be supplied to the electronic circuit 14 via the interrogator 60, which may transfer energy (e.g., electric voltage) to the indicator 274. The indicator 274 may be electrically coupled to the electronic circuit 14, such that energy may be provided to the electronic circuit 14 to engage the test. In still further embodiments, the component housing 152 may be removed from the housing 150 to perform a test. In such embodiments, the electronic circuit 14 may be physically coupled to a test device (e.g., a computer, a tablet, a mobile phone, or another suitable device), which may supply power and activate the test of the electronic circuit 14.

FIG. 7 is a perspective view of the component housing 152 showing the socket 260 that may receive the intermediate connector 212. When the component housing 152 is disposed in the opening 172, the socket 260 may align with the fourth opening 210. Therefore, the intermediate connector 212 may extend from the fourth opening 210 into the socket 260 to couple to the electronic circuit 14 and/or the memory 16. As discussed above, the intermediate connector 212 may also couple to the battery 12, thereby establishing the electrical pathway between the battery 12 and the electronic circuit 14 and/or the memory 16 as well as further isolate the electronic circuit 14 and/or the memory from the chamber 162 in which water may contact the battery 12. As shown in the illustrated embodiment of FIG. 7, the socket 260 may be offset from the opening 262 with respect to a lateral axis 278 extending parallel to a height 280 of the component housing 152. However, in other embodiments, the opening 262 and the socket 260 may be substantially coaxial (e.g., aligned along the lateral axis 278) to facilitate manufacturing of the component housing 152 (e.g., the housing 152 may be aligned with a drilling device one time to form both the opening 262 and the socket 260).

Figure 8:
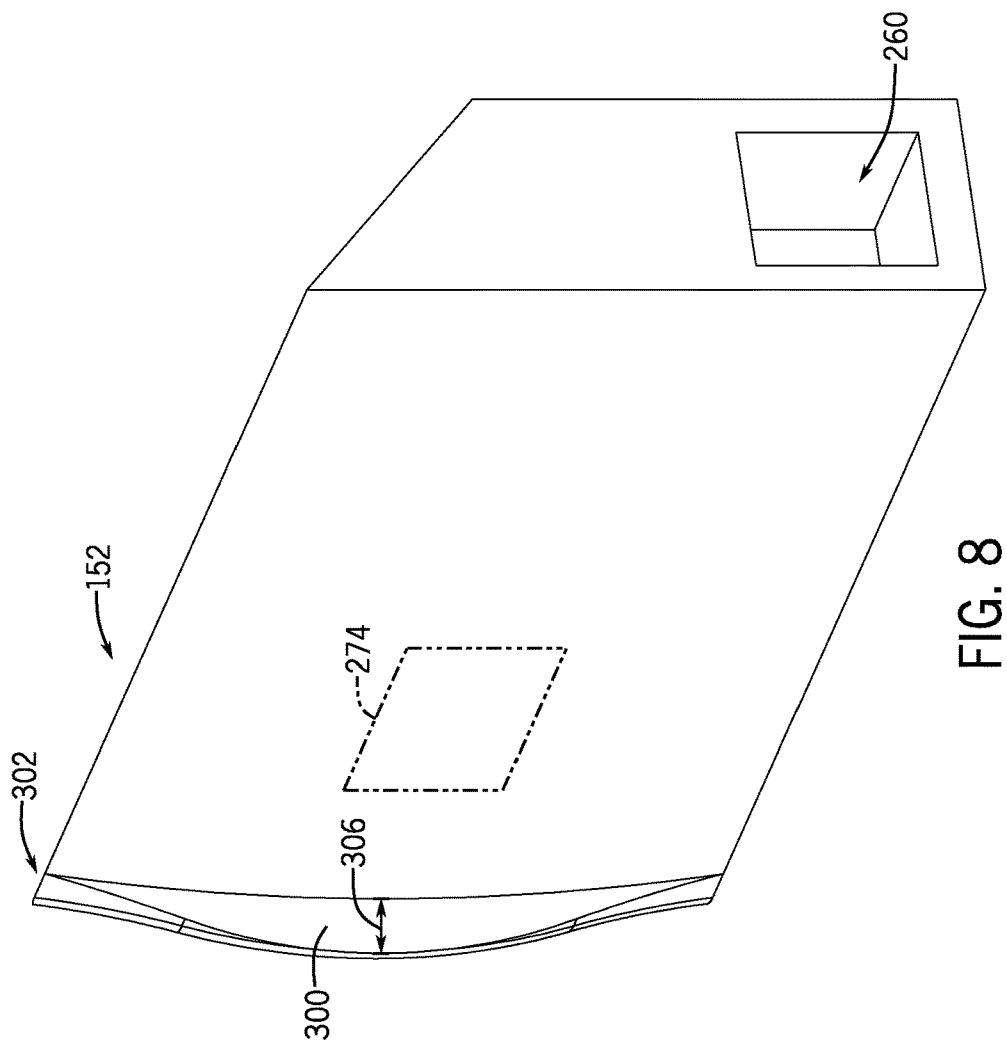
FIG. 8 is a perspective view of an embodiment of the component housing of FIG. 6 that may be configured to be disposed within the housing of FIGS. 3 and 4, in accordance with an aspect of the present disclosure.

As discussed above, the component housing 152 is modular with respect to the water detection device 10 and the housing 150. Therefore, the component housing 152 may include features that may facilitate insertion and/or removal of the component housing 152 from the opening 172. For example, FIG. 8 is a perspective view of the component housing 152 illustrating a handle 300 that may be utilized to insert and/or remove the component housing 152 from the opening 172. As shown in the illustrated embodiment of FIG. 8, the handle 300 may extend from a corner 302 of the component housing 152 to provide a structure that may be easily gripped so that the component housing 152 may be pushed and/or pulled from the opening 172. Additionally, when the component housing 152 is disposed within the opening 172 of the housing 150, the handle 300 may extend from a corner 304 (see, e.g., FIG. 3) of the housing 150, such that the handle 300 may still be gripped to facilitate removal of the component housing 152 from the opening 172. In some embodiments, the handle 300 may extend a distance 306 from the corner 302 (and/or the corner 304). The distance 306 may be between 0.01 centimeters (cm) and 10 cm, between 0.5 cm and 5 cm, or between 1 cm and 3 cm.

Figure 9:
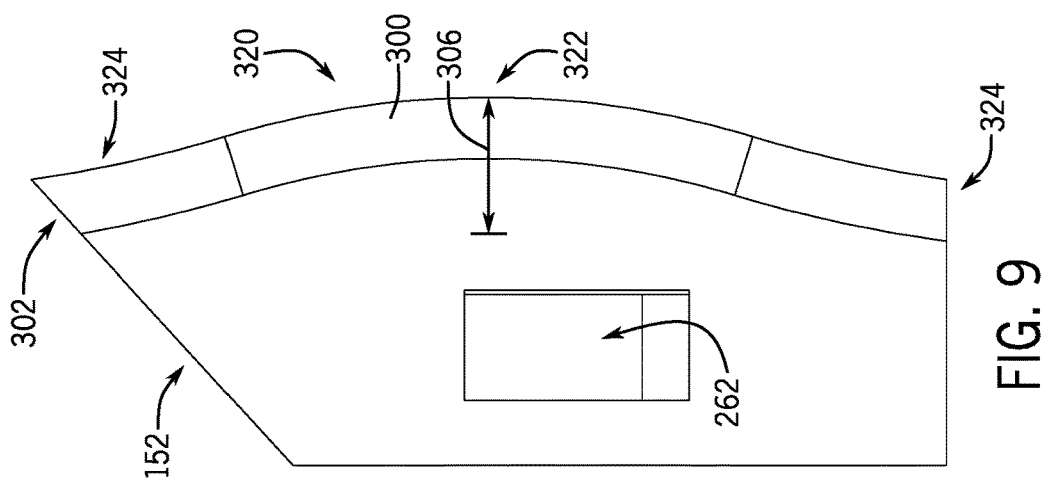
FIG. 9 is a plan view of an embodiment of the component housing of FIG. 6 that shows a shape of a handle, in accordance with an aspect of the present disclosure.

Further, FIG. 9 is a plan view of the component housing 152 illustrating a shape of the component housing 152 and the handle 300. For example, as shown in the illustrated embodiment of FIG. 9, the handle 300 includes a curved shape 320. In other words, the distance 306 in which the handle 300 extends from the corner 302 is greatest at a middle portion 322 of the corner 302 and is the smallest at ends 324 of the corner 302. In other embodiments, the handle 300 may include another suitable configuration, such as a straight line that includes a uniform distance 306 from the corner 302 between the ends 324 of the corner 302 (e.g., a uniform distance 306 along an entire length of the corner 302). In any case, the component housing 152 is configured to be received within the opening 172 of the housing 150, thereby securing the electronic circuit 14 and/or the memory 16 within the housing 150 as well as placing the electronic circuit 14 and/or the memory 16 in electrical communication with the battery 12.

As discussed above, the water detection device 10 may be configured to communicate with the electronic device 30 (e.g., via the electronic circuit) to provide information related to the water detection device 10 and/or to alert a user of a detection event. While the electronic device 30 may be any suitable electronic device, such as a computer, a tablet, a mobile phone, another portable electronic device, a server, another electronic device, or a combination thereof, the following description illustrates the electronic device 30 as a mobile phone. Additionally, the electronic device 30 may include software and/or programming that facilitates communication between the electronic device 30 and the water detection device 10. As a non-limiting example, the electronic device 30 may include an application (e.g., a phone app) that may be configured to communicate with, program, and/or perform other functions related to the water detection device 10. The user may then open the application and/or software when it is desired to perform a task, such as linking a new water detection device 10 to the user's account. Additionally, the application and/or software may provide alerts to the electronic device 30 to inform the user when a detection event occurs. FIGS. 10-14 illustrate schematic embodiments of user interfaces (e.g., displays) that the application and/or software may display to the user to interact and/or communicate with the water detection device 10.

Figure 10:
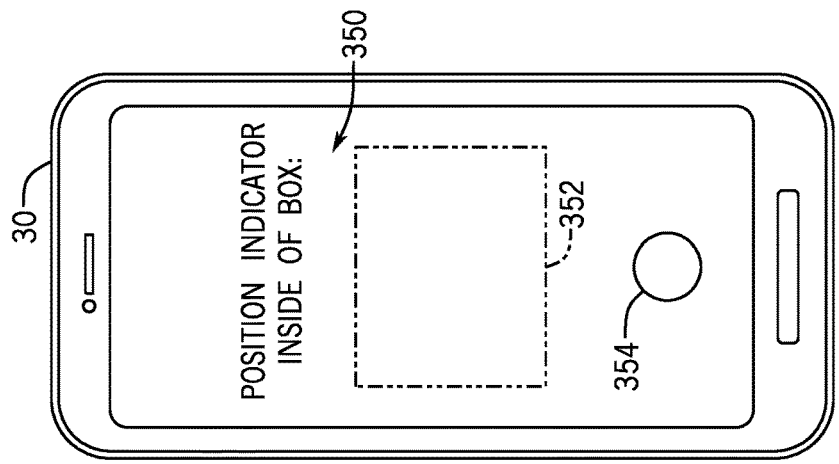
FIG. 10 is a schematic of an embodiment of a first user interface on an electronic device that may be utilized with the water detection device of FIG. 1, in accordance with an aspect of the present disclosure.

FIG. 10 is a schematic of an embodiment of a first display 350 that may be displayed on the electronic device 30 (e.g., via the application and/or software). As shown in the illustrated embodiment of FIG. 10, the first display 350 may prompt the user to position a frame 352 over the indicator 274 of the component housing 152 and/or the indicator 168 of the housing 150. More specifically, this may include positioning an image of the indicator 168 and/or the indicator 274 captured by a camera of the electronic device 30 within the frame 352 graphically presented in the first display 350. In some embodiments, the software and/or the application may automatically recognize the indicator 274 and/or the indicator 168 when the indicator 274 and/or the indicator 168 are positioned within the frame 352. In other embodiments, the user may be further prompted to take a picture of the indicator 274 and/or the indicator 168 for the software and/or application to recognize the indicator 274 and/or the indicator 168. For example, the user may engage a button 354 to activate image capture by a camera of the electronic device 30 and take a picture of the indicator 274 and/or the indicator 168.

In any case, the software and/or application may associate the electronic circuit 14 with the user's account (e.g., the user logs into the software before seeing the first display 350). Additionally, the software and/or application may connect the electronic circuit 14 to the electronic device 30 to enable the electronic circuit 14 to communicate with the electronic device 30 and provide a status and/or condition of the water detection device 10. For example, the electronic circuit 14 may be preprogrammed to connect to the network 22 (e.g., the Internet), such that the electronic circuit 14 may communicate with the electronic device 30 via the network 22. Additionally or alternatively, the software and/or application may enable the user to connect the electronic circuit 14 to the network 22. In some embodiments, the user may be able to scan more than one of the indicators 274 and/or the indicators 168 of multiple water detection devices 10 before the software and/or application proceeds to a second display 370 (see FIG. 11).

Figure 11:
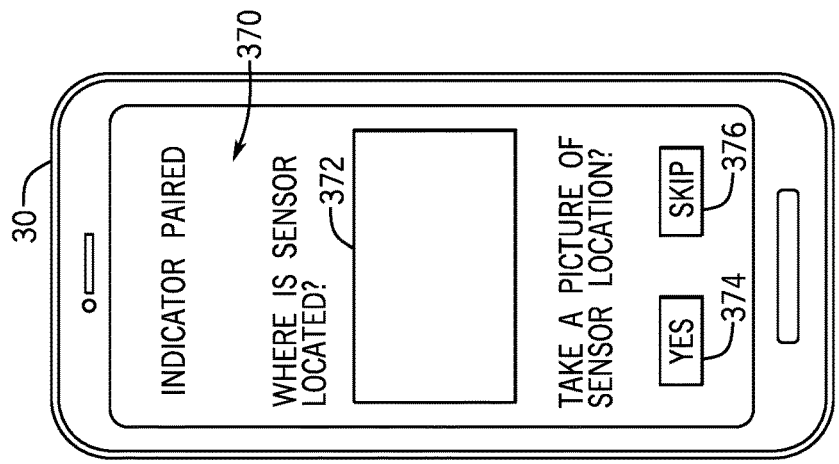
FIG. 11 is a schematic of an embodiment of a second user interface on an electronic device that may be utilized with the water detection device of FIG. 1, in accordance with an aspect of the present disclosure.

When the software and/or application recognizes the indicator 274 and/or the indicator 168 (e.g., pairs the indicator 274 and/or the indicator 168 with the electronic device 30), the software and/or application may prompt the user to provide a location of the water detection device 10. For example, FIG. 11 is a schematic of an embodiment of the second display 370 notifying the user that the indicator 274 and/or the indicator 168 has been recognized and paired with the electronic device 30. The second display 370 may also include an input box 372 that enables the user to input a location or position of the water detection device 10. In some embodiments, the input box 372 may receive an input from the user via a keyboard of the electronic device 30 that inputs text related to the position of the water detection device 10. Additionally or alternatively, the input box 372 may receive the input using another suitable technique (e.g., a voice-recognition device).

Further, the second display 370 may provide the user with an option to take a picture of the water detection device 10 in the location and/or a picture of the location where the water detection device 10 will be positioned. For example, the user may activate a button 374 if the user decides to take a picture of the location (e.g., under a kitchen sink) in which the water detection device 10 will be positioned. Further, the user may take a picture of the location with the water detection device 10 hidden from view (e.g., behind a door, cabinet, or wall) and have the option to select an indicator (e.g., an icon) to position on the image to designate the actual position of the water detection device 10. Should the user select to take the picture, the software and/or the application may provide the user with the location and/or a picture of the location of the water detection device 10 when a detection event occurs. However, the user may also select to activate a second button 376 if the user would like to skip taking a picture of the location of the water detection device 10 and instead use only the input from the input box 372 to determine the location of the water detection device 10 when the detection event occurs.

Figure 13:
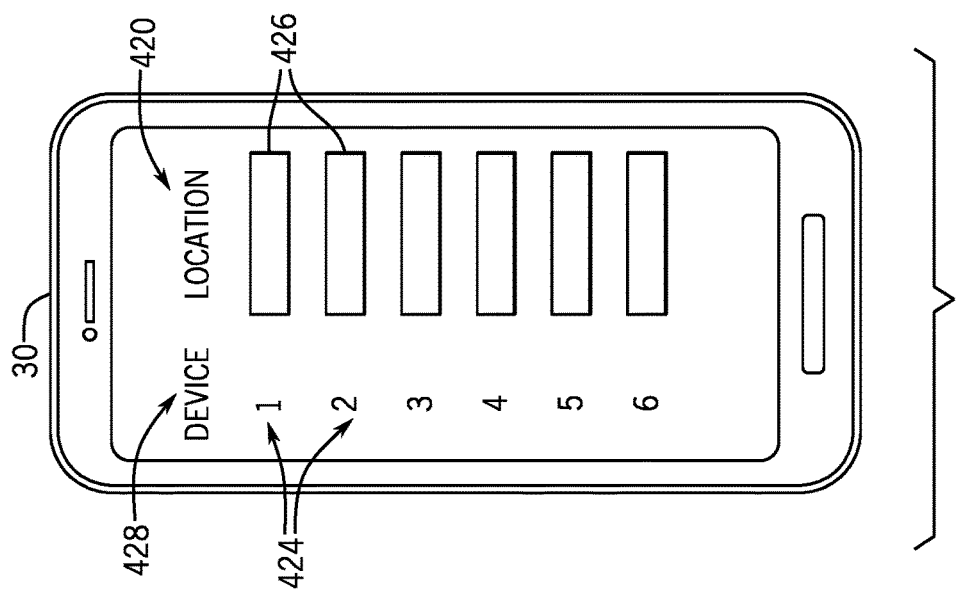
FIG. 13 is a schematic of an embodiment of a fourth user interface on an electronic device that may be utilized with the water detection device of FIG. 1, in accordance with an aspect of the present disclosure.

In some embodiments, the user may change the location of the water detection device 10 by directing the software and/or application to the second display 370 (e.g., by activating a particular water detection device 10 in a summary list, such as shown in FIG. 13 discussed below). Further, the software and/or application may store the location of the water detection device 10, which may be utilized to track previous detection events at a particular location. Additionally, the software and/or application may be configured to automatically establish an insurance claim upon the occurrence of a detection event (e.g., the software and/or application may be linked to the user's insurance).

Figure 12:
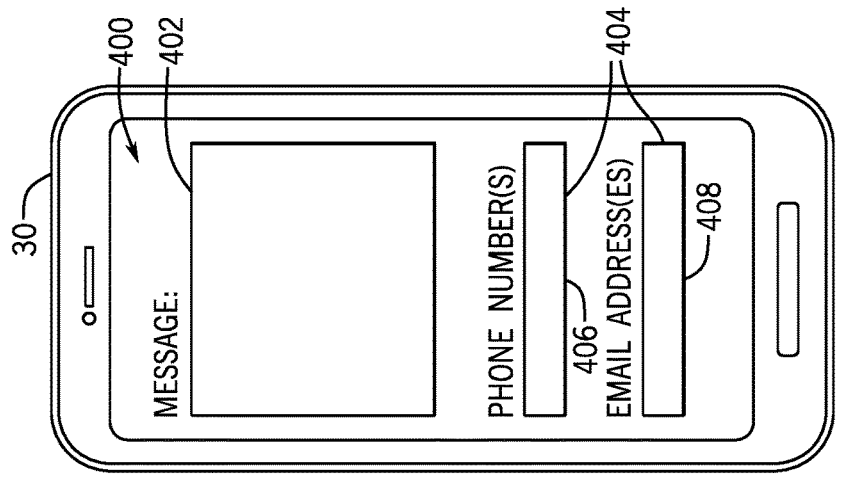
FIG. 12 is a schematic of an embodiment of a third user interface on an electronic device that may be utilized with the water detection device of FIG. 1, in accordance with an aspect of the present disclosure.

The software and/or the application may provide the user with a message and/or alert when a detection event occurs. For example, FIG. 12 is a schematic of a third display 400 that may enable the user to input a personalized message that may be sent to the user when a detection event occurs. For example, the third display 400 may include a first input box 402 that may enable the user to create a personalized message that may be sent to the user upon a detection event. As discussed above, the input box 402 may receive the message from the user via a keyboard of the electronic device 30 that inputs text. Additionally or alternatively, the input box 402 may receive the input using another suitable technique (e.g., a voice-recognition device). For example, the message may be in the form of a voice message recorded by the user, electronically synthesized, or generated using another suitable method. In other embodiments, the input box 402 may be a pull-down box that allows the user to select a predetermined message that is part of the software and/or the application.

Further, the third display 400 may include one or more second input boxes 404 for the user to enter a phone number 406, an email address 408, an IP address, a URL, and/or other suitable information related to where the message is to be sent. In some embodiments, the user may input multiple addresses into each of the one or more second input boxes 404. For example, the user may desire for the message to be sent to the electronic device 30 of the user as well as to an electronic device of a neighbor, family member, coworker, or another person. The message information and address information may be transmitted to the electronic circuit 14 through a wireless connection such as radio-frequency identification technology, Wi-Fi, Bluetooth, near field communication, Zigbee, or another suitable wireless communication technique. When a detection event occurs, the electronic circuit 14 may then send the message through the network 22 (e.g., the Internet) to the address or addresses specified in the one or more input boxes 404. Thus, the user can program the electronic circuit 14 to send a custom message that may report a detection event by the water detection device 10 (e.g., a leak detection event) as well as one or more electronic addresses where the message is sent. In some embodiments, text messages may be sent in more than one form, such as short message service (SMS), multi-media messages (MMS), email, or another suitable electronic messaging system.

In some embodiments, a fourth display 420 may be configured to allow entries of a unique number corresponding to a respective water detection device 10, such as a device number 424 that corresponds to a physical location 426 of the respective water detection device 10. For example, FIG. 13 is a schematic of an embodiment of the fourth display 420 having information relating to one or more water detection devices 10 in a table 428. As shown in the illustrated embodiments, the table 428 may display to the user the locations 426 of the water detection devices 10 as well as the corresponding unique device number 424. Therefore, the user may direct the software and/or application to the fourth display 420 to view a simple, concise list of each of the water detection devices 10 and their corresponding location 426. In some embodiments, the device number 424 and physical location 426 information may be incorporated into the message sent to the user by the electronic circuit 14 when a detection event occurs (e.g., a leak detection event). Additionally, the user may be able to select one of the water detection devices 10 displayed in the table 428 and retrieve a status of the respective water detection device 10 and/or to change the location of the respective water detection device 10. In some embodiments, the user may also activate a test to determine the condition of the respective water detection device 10.

Further still, the user may be able to view a fifth display 450, which may illustrate a position of each of the water detection devices 10 on a map or floor plan 452. As shown in the illustrated embodiment of FIG. 14, one of the water detection devices 10 may be disposed under a first floor bathroom sink 454 and another one of the water detection devices 10 may be disposed under a kitchen sink 456. Each of the water detection devices 10 may be represented on the map or floor plan 452 by a respective icon 458 positioned near an icon representing the physical object near where the sensor is located (e.g., a sink, toilet, shower, bath, hot tub, water heater, boiler, appliances).

In some embodiments, the user may be able to develop the map or floor plan 452 by sketching various lines 460 designating walls of a structure 462 in which the one or more water detection devices 10 may be disposed. The user may also select predetermined icons 464 that designate sinks, pipes, washing machines, dishwashers, water heaters, bathtubs, toilets, showers, boilers, refrigerators, hot tubs, and/or other appliances, devices, and structures that may utilize or dispense water. The user may then drag and drop such predetermined icons 464 in their respective positions within the structure 462. For example, the predetermined icons 464 may include dashed lines before the user places the predetermined icons 464 in the desired position within the map or floor plan 452. Finally, the user may drag and drop the respective icons 458 for the water detection devices 10 in their respective positions within the structure and relative to the various appliances, devices, and structures designated by the icons 464. In some embodiments, the fifth display 450 may include multiple pages, where each page designates a floor, room, and/or hallway of the structure 462. In some embodiments, the user may select a respective water detection device 10 and obtain information (e.g., a status and/or a condition) related to the respective water detection device 10. As discussed above, the user may activate a test to determine the condition of the water detection device 10 upon selecting the respective water detection device 10 from the map or floor plan 452.

FIG. 15 is a flow chart of an embodiment of a method 500 for determining a detection event and reporting the event to the user. At block 502, the water detection device 10 having the battery 12 and the electronic circuit 14 may be provided. At block 504, the user may dispose the water detection device 10 in a predetermined position and link the water detection device 10 (as well as corresponding information related to the water detection device 10) with the electronic device 10 (e.g., via the software and/or the application). At block 506, water may come into contact with the water detection device 10, such that the battery 12 is activated and the water detection device establishes a detection event. At block 508, the detection event may be reported to the designated recipient (e.g., the electronic device 30 and/or the addresses input into the one or more second input boxes 404). The software and/or the application may then send the message to the designated recipient (e.g., the electronic device and/or the one or more addresses input into the one or more second input boxes 404).

While only certain features of the disclosure have been illustrated and described herein, many modifications and changes will occur to those skilled in the art. It is, therefore, to be understood that the appended claims are intended to cover all such modifications and changes as fall within the true spirit of the invention.

The invention claimed is:
1. A water detection device, comprising:
a water-activated battery configured to switch from a dormant condition to an active condition upon contact with water, such that the water-activated battery supplies an electrical voltage upon contact with the water;
an electronic circuit configured to receive the electrical voltage from the water-activated battery, wherein the electronic circuit is configured to communicate with an external, electronic device via one or more wireless communication techniques when the electronic circuit is powered by the electrical voltage, and wherein communication between the electronic circuit and the external, electronic device is an uninterrupted communication when the electronic circuit is receiving the electrical voltage from the water-activated battery;
an additional battery configured to periodically supply an additional electrical voltage to the electronic circuit, such that communication between the electronic circuit and the external electronic device is intermittent when the water-activated battery is in the dormant condition; and
a housing configured to receive the water-activated battery and the electronic circuit, wherein the housing comprises passageways configured to facilitate movement of the water into the housing and toward the battery.

2. The water detection device of claim 1, comprising a hub, wherein the electronic circuit is configured to communicate with the external, electronic device via the hub.

3. The water detection device of claim 2, wherein the hub comprises a display configured to indicate a status of the hub.

4. The water detection device of claim 2, wherein the hub comprises a visual indicator configured to indicate that the water-activated battery is in the active condition and that a detection event occurred.

5. The water detection device of claim 4, wherein the hub is configured to send an alert to the external, electronic device when the detection event occurs.

6. The water detection device of claim 2, comprising a local monitoring entity coupled to the hub via a network, wherein the local monitoring entity is configured to store detection event reports sent from the electronic circuit to the hub.

7. The water detection device of claim 6, wherein the local monitoring entity comprises a firewall, a server, a database, or a combination thereof.

8. The water detection device of claim 6, wherein the local monitoring entity is an interrogator configured to supply an interrogation electrical voltage to the electronic circuit, such that the electronic circuit communicates with the local monitoring entity upon supply of the interrogation electrical voltage.

9. The water detection device of claim 8, wherein the local monitoring entity supplies the interrogation electrical voltage to the electronic circuit to determine a status of the water detection device.

10. A water detection device, comprising:
a water-activated battery to switch from a dormant condition to an active condition upon contact with water, such that the water-activated battery supplies an electrical voltage upon contact with the water;
an electronic circuit configured to receive the electrical voltage from the water-activated battery, wherein the electronic circuit is configured to communicate with an external, electronic device via one or more wireless communication techniques when the electronic circuit is powered by the electrical voltage, and wherein communication between the electronic circuit and the external, electronic device is an uninterrupted communication when the electronic circuit is receiving the electrical voltage from the water-activated battery;
an additional battery configured to periodically supply an additional electrical voltage to the electronic circuit, such that communication between the electronic circuit and the external electronic device is intermittent when the water-activated battery is in the dormant condition; and
a housing configured to receive the water-activated battery, the electronic circuit, and the additional battery, wherein the housing comprises passageways configured to facilitate movement of the water into the housing and toward the battery.

11. The water detection device of claim 10, wherein the electronic circuit is configured to transmit a signal to an IP address, a URL, an email address, a telephone number, a monitoring station, or any combination thereof.

12. The water detection device of claim 10, wherein the electronic circuit is configured to communicate with the external, electronic device via Bluetooth.

13. The water detection device of claim 10, wherein the electronic circuit is configured to communicate with the external, electronic device via radio-frequency identification technology.

14. A method, comprising:
sending intermittent communications between an electronic circuit of a detection device and an external, electronic device when a water-activated battery electrically coupled to the electronic circuit is in a dormant condition;
activating the water-activated battery to switch from the dormant condition to an active condition upon exposure of the water-activated battery to water;
supplying an electrical voltage from the water-activated battery to the electronic circuit when the water-activated battery is in the active condition; and
sending uninterrupted communications between the electronic circuit and the external, electronic device when the water-activated battery is in the active condition.

15. The method of claim 14, wherein sending the intermittent communications between the electronic circuit and the external, electronic device when the water-activated battery is in the dormant condition comprises intermittently supplying additional electrical voltage to the electronic circuit from an additional power source of the detection device.

16. The method of claim 14, wherein sending the intermittent communications between the electronic circuit and the external, electronic device when the water-activated battery is in the dormant condition comprises intermittently supplying additional electrical voltage to the electronic circuit from an additional power source external to the detection device.

17. The method of claim 16, wherein the additional power source external to the detection device comprises an interrogator.

18. A water detection device, comprising:
a water-activated battery configured to switch from a dormant condition to an active condition upon contact with water, such that the water-activated battery supplies an electrical voltage upon contact with the water;
an electronic circuit configured to receive the electrical voltage from the water-activated battery, wherein the electronic circuit is configured to communicate with an external, electronic device via one or more wireless communication techniques when the electronic circuit is powered by the electrical voltage, and wherein communication between the electronic circuit and the external, electronic device is an uninterrupted communication when the electronic circuit is receiving the electrical voltage from the water-activated battery;
an additional battery configured to continuously supply an additional electrical voltage to the electronic circuit, such that communication between the electronic circuit and the external electronic device is uninterrupted when the water-activated battery is in the dormant condition; and
a housing configured to receive the water-activated battery and the electronic circuit, wherein the housing comprises passageways configured to facilitate movement of the water into the housing and toward the battery.

19. The water detection device of claim 18, wherein the electronic circuit communicates a status of the electronic circuit to the external, electronic device via the uninterrupted communication.

* * * * *

UNITED STATES PATENT AND TRADEMARK OFFICE
CERTIFICATE OF CORRECTION

PATENT NO.        : 10,119,884 B1  
APPLICATION NO.   : 15/636270  
DATED             : November 6, 2018  
INVENTOR(S)       : Bradly Jay Billman et al.

Page 1 of 1

It is certified that error appears in the above-identified patent and that said Letters Patent is hereby corrected as shown below:

On the Title Page

1. In Item (71), under "Applicant", in Column 1, Line 1, delete "Automoblie" and insert -- Automobile --, therefor.

2. In Item (72), under "Inventors", in Column 1, Line 4, delete "Cellina, TX" and insert -- Celina, TX --, therefor.

In the Specification

3. In Column 2, Line 26, delete "DRAWINGS" and insert -- BRIEF DESCRIPTION OF DRAWINGS --, therefor.

4. In Column 9, Line 21, delete "sidewall s 154," and insert -- sidewalls 154, --, therefor.

5. In Column 10, Lines 30-31, delete "opening 182" and insert -- opening 172 --, therefor.

6. In Column 11, Line 64, delete "150." and insert -- 150). --, therefor.

7. In Column 17, Line 36, delete "capture by" and insert -- captured by --, therefor.

Signed and Sealed this  
Twenty-fifth Day of June, 2019

Andrei Iancu  
*Director of the United States Patent and Trademark Office*